United States Patent
Pei

(10) Patent No.: US 7,894,897 B1
(45) Date of Patent: Feb. 22, 2011

(54) IMPLANTABLE CARDIAC STIMULATION DEVICE PROVIDING ENHANCED CAPTURE THRESHOLD MANAGEMENT IN THE PRESENCE OF FUSION BEATS AND METHOD

(75) Inventor: Xing Pei, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 962 days.

(21) Appl. No.: 11/417,966

(22) Filed: May 3, 2006

(51) Int. Cl.
*A61N 1/37* (2006.01)

(52) U.S. Cl. .................. 607/9; 607/25; 607/26; 607/27

(58) Field of Classification Search .............. 607/9, 607/25, 26, 27
See application file for complete search history.

(56) References Cited

U.S. PATENT DOCUMENTS

| | | | | |
|---|---|---|---|---|
| 4,686,988 A | 8/1987 | Sholder | ............ | 128/419 PT |
| 4,708,142 A | 11/1987 | DeCote, Jr. | ............ | 128/419 PT |
| 4,729,376 A | 3/1988 | DeCote, Jr. | ............ | 128/419 PT |
| 4,878,497 A * | 11/1989 | Callaghan et al. | ............ | 607/26 |
| 4,969,464 A | 11/1990 | Callaghan et al. | ............ | 128/419 PG |
| 4,969,467 A | 11/1990 | Callaghan et al. | ............ | 128/419 PG |
| 5,350,410 A | 9/1994 | Kleks et al. | ............ | 607/28 |
| 5,534,016 A * | 7/1996 | Boute | ............ | 607/9 |
| 6,038,474 A | 3/2000 | Zhu et al. | ............ | 607/9 |
| 6,317,633 B1 * | 11/2001 | Jorgenson et al. | ............ | 607/28 |
| 6,324,427 B1 | 11/2001 | Florio | ............ | 607/28 |
| 7,424,323 B1 * | 9/2008 | Reiss et al. | ............ | 607/9 |
| 2003/0050671 A1 | 3/2003 | Bradley | ............ | 607/27 |
| 2004/0127949 A1 | 7/2004 | Kim et al. | ............ | 607/27 |
| 2004/0127950 A1 | 7/2004 | Kim et al. | ............ | 607/27 |

FOREIGN PATENT DOCUMENTS

| | | |
|---|---|---|
| EP | 1 291 038 A2 | 3/2003 |
| EP | 1 291 038 A3 | 1/2005 |

* cited by examiner

*Primary Examiner* — Scott M Getzow
*Assistant Examiner* — Joseph M Dietrich

(57) ABSTRACT

An implantable cardiac stimulation device recognizes and accommodates fusion beats without compromising autocapture or threshold searches. The device comprises a pulse generator that provides first and second pacing pulses to a chamber of a heart. The first pacing pulses have a normal operating output level and the second pacing pulses have an output level sufficient to assure capture. The device further comprises a fusion beat predicting circuit that predicts when a next paced event of the chamber will likely be a fusion beat and a fusion beat control that causes the pulse generator to provide a second pacing pulse to the chamber in response to the fusion beat predicting circuit predicting that a next paced event will likely be a fusion beat. Thereafter, the fusion beat is confirmed.

20 Claims, 4 Drawing Sheets

IMPLANTABLE CARDIAC STIMULATION DEVICE PROVIDING ENHANCED CAPTURE THRESHOLD MANAGEMENT IN THE PRESENCE OF FUSION BEATS AND METHOD

FIELD OF THE INVENTION

The present invention generally relates to an implantable cardiac stimulation device that provides electrical therapy to a patient's heart. The present invention more particularly relates to such a device that performs autocapture while recognizing and managing fusion beats.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker is comprised of two major components. One component is the device itself which includes pulse generator circuitry that generates the pacing stimulation pulses, other circuitry that senses cardiac activity, and a power cell or battery. The other component is the lead, or leads, having electrodes which electrically couple the pacemaker to the heart. A lead may provide both unipolar and bipolar pacing polarity electrode configurations. In unipolar pacing, the pacing stimulation pulses are applied between a single electrode carried by the lead, in electrical contact with the desired heart chamber, and the pulse generator case. Usually the electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events represented as P waves on the surface electrocardiogram (ECG) and intrinsic ventricular events represented as R waves on the surface ECG. The pacemaker, however, does not use the surface ECG electrical events but uses the signal as identified inside the heart. This is termed an electrogram. It would be an atrial EGM (AEGM) for the native atrial depolarization and a ventricular EGM (VEGM) for a native ventricular depolarization. By monitoring such AEGM and VEGM, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

The energies of the applied pacing pulses are selected to be above the pacing energy stimulation threshold of the respective heart chamber to cause the heart muscle of that chamber to depolarize or contract. If an applied pacing pulse has an energy below the pacing energy stimulation threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the pacing energy stimulation threshold.

However, it is also desirable to employ pacing energies which are not exorbitantly above the stimulation threshold. The reason for this is that pacemakers are implanted devices and rely solely on battery power. Using pacing energies that are too much above the stimulation threshold would result in early depletion of the battery and hence premature device replacement. Prior to autocapture, the capture threshold would be assessed at the periodic follow-up visits with the physician and the output of the pacemaker adjusted (programmed) to a safety margin that was appropriate based on the results of that evaluation. However, capture thresholds may change between scheduled follow-up visits with the physician. A refinement of the technique of periodic capture threshold measurements by the physician was the automatic performance of capture threshold assessment and the automatic adjustment of the output of the pulse generator. Capture threshold may be defined in terms of pulse amplitude, either voltage or current, pulse duration or width, pulse energy, pulse charge or current density. The parameters that can be easily adjusted by the clinician are pulse amplitude and pulse width. With the introduction of autocapture, the implanted pacing system may periodically and automatically assesses the capture threshold and then adjusts the delivered output. It also monitors capture on a beat-by-beat basis such that a rise in capture threshold will be recognized allowing the system to compensate by delivery initially of higher-output back-up or safety pulses and then incrementing the output of the primary pulse until stable capture is again demonstrated. The output amplitude of the pacing stimulus is set slightly above the measured capture threshold minimizing battery drain while the patient is protected by the significantly higher output back-up safety pulse. These evaluations are often referred to as autocapture tests or simply autocapture.

As is well known in the art, the stimulation threshold of a heart chamber can, for various reasons, change over time. Hence, pacemakers that incorporate autocapture are generally able to periodically and automatically perform autocapture tests. In this way, the variations or changes in stimulation threshold can be accommodated.

When a pacing pulse is effective in causing depolarization or contraction of the heart muscle, it is referred to as "capture" of the heart. Conversely, when a pacing pulse is ineffective in causing depolarization or contraction of the heart muscle, it is referred to as "lack of capture" or "loss of capture" of the heart.

When a pacemaker performs an autocapture test, its pulse generator applies a succession of primary pacing pulses to the heart at a basic rate. The output of the primary pulse is progressively reduced. In one known system, there will be a minimum of two consecutive pulses at a given energy before the output associated with the primary pulse is reduced or increased. The output of successive primary pacing pulses is reduced by a known amount and capture is verified following each pulse. If a primary pulse results in loss of capture, a backup or safety pulse is applied to sustain heart activity. If there is loss of capture associated with the primary pulse on two successive cycles, this is interpreted as being subthreshold. At that time, the output associated with the primary pulse is progressively increased in small increments until capture is confirmed on two consecutive primary pulses. This, of course, is but one example. As is known in the art, a single pulse or any number of pulses may be used to establish the capture threshold. The lowest output setting that results in capture on consecutive pulses starting from a low value where there is loss of capture is defined as the capture threshold. A most recent system then automatically adjusts the output with a working margin of an additional 0.25 Volts. In these methods, capture may be verified by detecting the evoked response associated with the output pulse, the T-waves or repolarization waves associated with the electrical depolarization, mechanical heart contraction, changes in cardiac blood volume impedance, or another signature of a contracting chamber.

Fusion and pseudo-fusion beats are commonly encountered in implantable cardiac pacing systems where a native atrial or ventricular intrinsic activation occurs at the same time or within a small window prior to the delivery of a pacing pulse to the same chamber. Accurate assessment of capture threshold in the presence of fusion and pseudo-fusion is a challenge. Fusion beats can confuse capture threshold management algorithms during their normal operation and during the capture threshold search. For example, fusion beats can produce a false-negative result or a false positive result. A false-negative results when a stimulus is determined to be sub-threshold when in fact capture occurred. When a fusion beats occurs, the intrinsic cardiac signal obscures the evoked response, causing the evoked potential to go undetected. In contrast, a pseudo-fusion beat can result in a false-positive classification. Pseudo-fusion occurs when a pacing stimulus occurs coincident with the intrinsic depolarization. With pseudo-fusion beats, however, the pacing pulse does not capture the heart but is detected as capture because the system incorrectly classifies the intrinsic waveform as an evoked response.

If the pacing system paces the heart without evaluating the evoked response, the fusion/pseudo-fusion beats have no effect on either the heart or the pacing system. However, if the pacing system needs to evaluate the evoked responses of the pacing pulse, the fusion/pseudo-fusion distorts the evoked potential such that a false-capture indication can result. When the system has a false-negative capture indication, the system delivers a backup pulse. This can be an undesired behavior, especially in a very sensitive atrium where a backup pulse might induce atrial fibrillation. During a threshold search, false-positive or false-negative capture indications can result in false capture threshold assessment with the resulting capture threshold being either above or below the real capture threshold. For those algorithms which only assess capture threshold periodically instead of on a beat by beat basis, a false capture threshold assessment below the real capture threshold can be catastrophic, since the system may not provide enough stimulus energy to capture the heart. As used hereinafter, the term "fusion beat" will be used to denote both a fusion beat and a pseudo-fusion beat unless a contrary intent is indicated.

Hence, there is a need in the art for an implantable cardiac stimulation device capable of recognizing and responding to fusion beats in such a manner that such fusion beats do not disrupt normal device operation or capture threshold assessment. The present invention addresses these and other issues.

SUMMARY OF THE INVENTION

What is described is an implantable cardiac stimulation device comprising a pulse generator that provides first and second pacing pulses to a chamber of a heart. The first pacing pulses have a normal operating output level and the second pacing pulses have an output level greater than the normal operating output level. The device further comprises a fusion beat predicting circuit that predicts when a next paced event of the chamber will likely be a fusion beat and a fusion beat control that causes the pulse generator to provide a second pacing pulse to the chamber in response to the fusion beat predicting circuit predicting that a next paced event will likely be a fusion beat.

The output level of the second pacing pulses is sufficient to assure capture. The device may further comprise a sensing circuit that generates an electrogram signal representing activity of the chamber, the fusion beat predicting circuit may obtain a signal sample of the electrogram signal prior to the next paced event and compare the signal sample to a threshold to predict when a next paced event of the chamber will likely be a fusion beat. The fusion beat predicting circuit may establish a sampling window prior to each next paced event, determine a sampling window mean potential baseline and sampling window mean potential maximum deviation, and determine the threshold from the sampling window mean potential baseline and sampling window mean potential maximum deviation.

The device may further comprise a fusion beat confirmation circuit that confirms the predicted fusion beat after the second pacing pulse is provided to the chamber. The fusion beat confirmation circuit may confirm the predicted fusion beat based upon T wave morphology.

The device may further comprise a pacing parameter modifier that modifies pacing parameters of the device when the confirmation circuit confirms a predetermined number of consecutive fusion beats. The pacing parameter modifier may modify, for example, AV/PV interval and/or pacing rate.

The fusion beat control may cause the pulse generator to provide a first pacing pulse to the chamber in response to the fusion beat predicting circuit predicting that a next paced event will likely not be a fusion beat.

According to another embodiment, an implantable cardiac stimulation device comprises a pulse generator that provides first and second pacing pulses to a chamber of a heart with the first pacing pulses having a normal operating output level and the second pacing pulses having an output level greater than the normal operating output level and sufficient to assure capture. The device further comprises a fusion beat predicting circuit that predicts when a next paced event of the chamber will likely be a fusion beat and a fusion beat control that causes the pulse generator to provide a second pacing pulse to the chamber in response to the fusion beat predicting circuit predicting that a next paced event will likely be a fusion beat and to provide a first pacing pulse to the chamber in response to the fusion beat predicting circuit predicting that a next paced event will likely not be a fusion beat.

In accordance with a further embodiment, a method for use in an implantable cardiac stimulation device comprises predicting, prior to a next paced event in a chamber of a heart, if the next paced event is likely to be a fusion beat and providing the chamber of the heart with an exceptional pacing pulse of sufficient output to assure capture if the next paced event is predicted to likely be a fusion beat.

The method may further comprise providing a normal pacing pulse having a normal operating output to the chamber in response to failing to predict that a next paced event will likely be a fusion beat.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description includes the best mode presently contemplated for practicing the invention. This description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Figure 1:
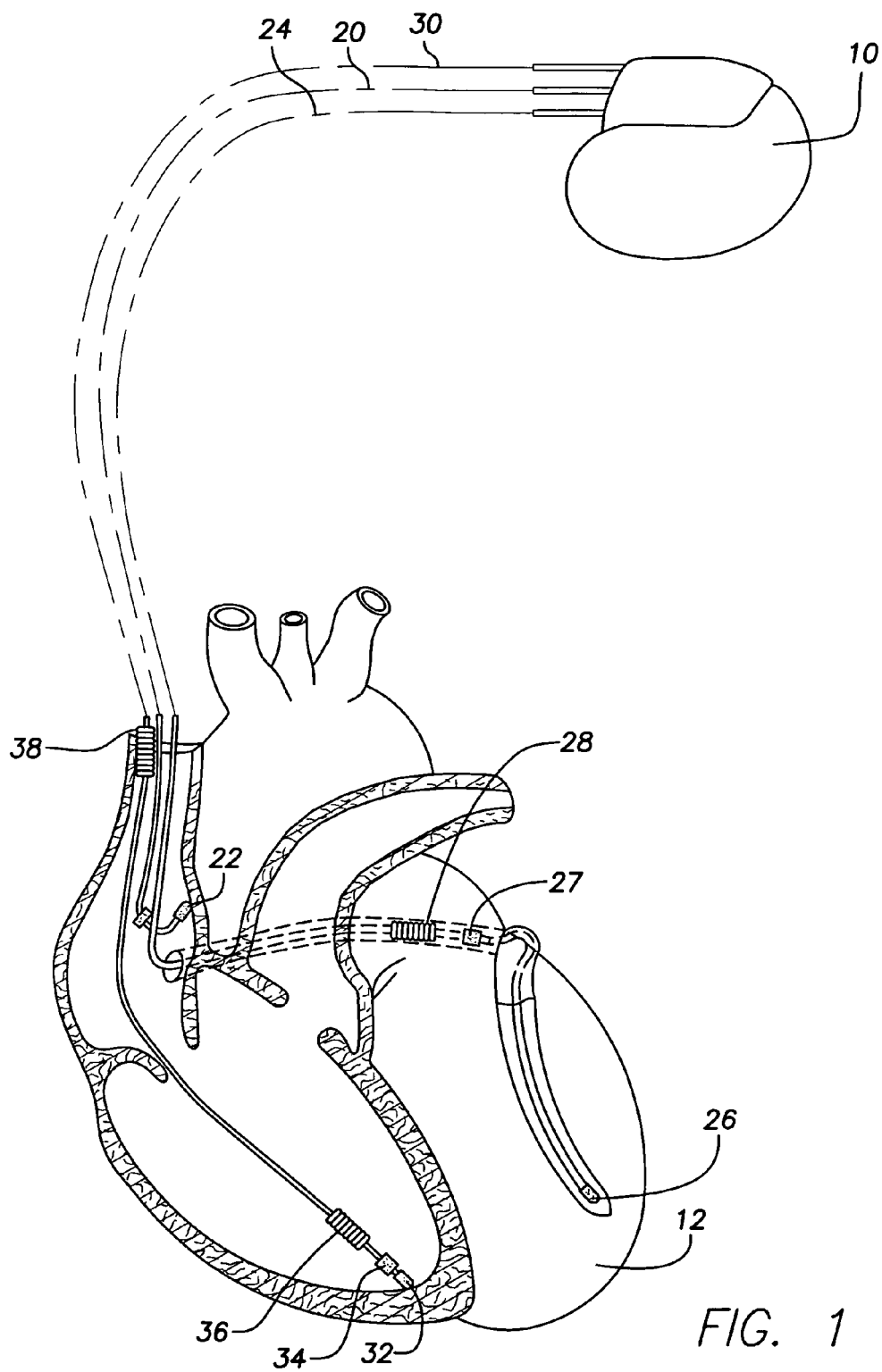
FIG. 1 is a simplified diagram illustrating an implantable stimulation device according to an embodiment of the invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/ or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
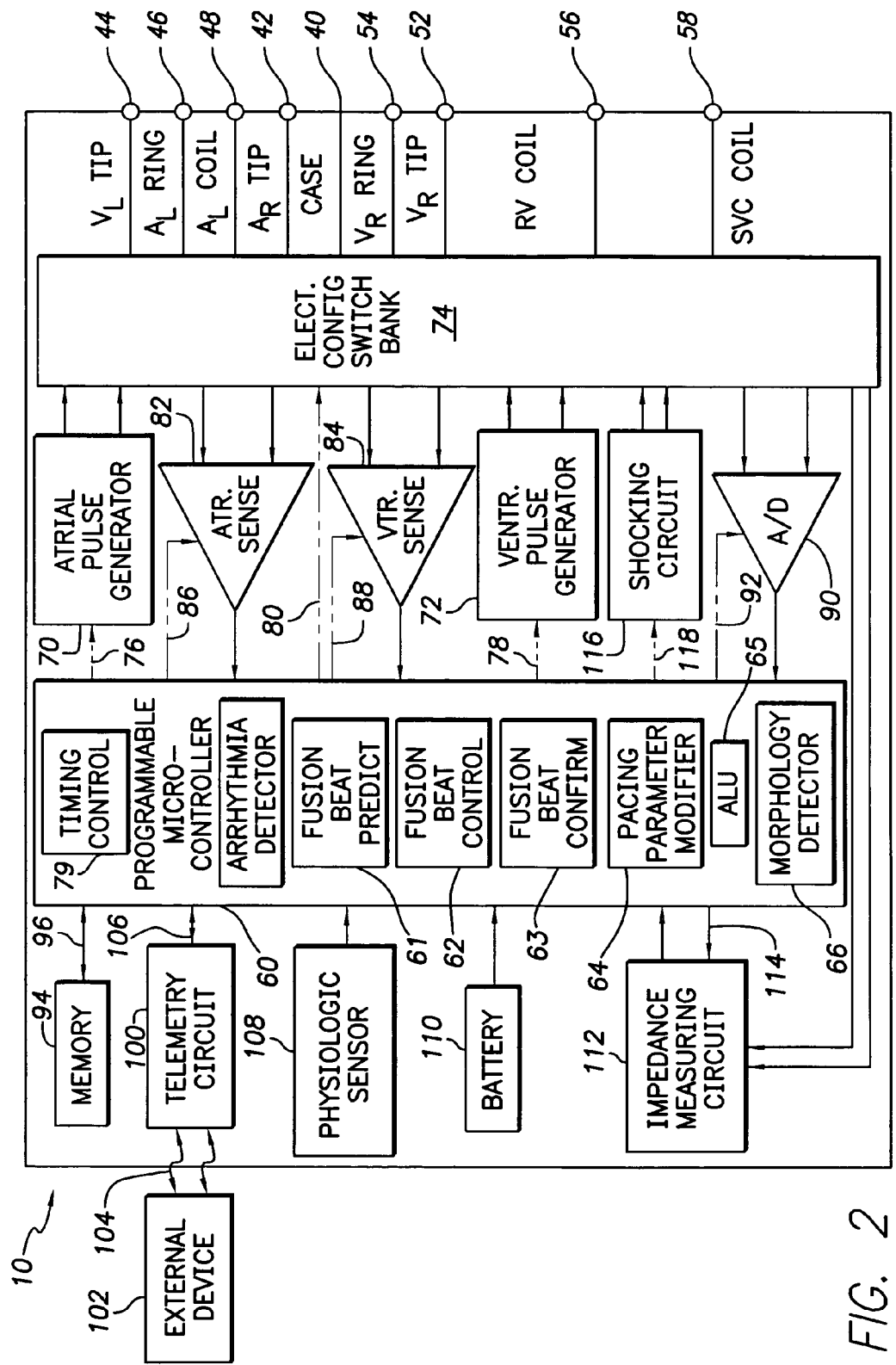
FIG. 2 is a functional block diagram of the implantable stimulation device of FIG. 1 illustrating the basic elements thereof for providing cardioversion, defibrillation and pacing stimulation in four chambers of the heart and for implementing an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. Further, and according to this embodiment, each of the pulse generators 70 and 72 is configured to provide both a normal pacing pulse having a regularly operating output and an exceptional pacing pulse having an output sufficient to cause capture for limited use when a next paced event is found to be likely to be a fusion beat. For this, the type of pacing pulse is selected by a fusion beat control 62, to be described subsequently.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram (EGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. As will be seen subsequently, the data acquisition system may be used to advantage in implementing this embodiment be providing an electrogram signal representing cardiac activity of a desired chamber (a ventricle and/or an atrium) for use in deriving threshold constants for use in predicting the likelihood of a fusion beat and morphologic analysis for fusion beat confirmation.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention. Furthermore, while the present invention is particularly useful during capture detection and threshold assessment, it may be employed at other times to advantage. Hence, it must be understood that the invention is not intended to be limited to capture detection and threshold assessment but is intended to extend to all applications where fusion beats are need of management.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as are known in the art.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Turning now more particularly to this embodiment of the invention, it addresses the fusion/pseudo-fusion issues by evaluating the intrinsic EGM signal provided by the data acquisition system 90 just before the device 10 is scheduled to deliver a pacing pulse and by determining the pacing pulse amplitude according to the evaluation result. The system then adjusts the pacing timing based on the programmed options.

A fusion or pseudo-fusion beat occurs when the chamber (ventricle or atrium) where the pacing electrode is located is depolarized simultaneously by spontaneous and pacemaker induced activity. A fusion beat is often narrower than a pure paced beat and can exhibit various morphologic features depending on the relative contribution of the two foci to the depolarization. Pseudo-fusion beat consists of the superimposition of an ineffectual pacemaker stimulus on a native depolarization originating from a single foci.

When a fusion or pseudo-fusion beat is going to occur, there is an intrinsic activity potential due to intrinsic activation of the cells. These intrinsic signal amplitudes are below the detection threshold of the system. Therefore they are not able to cause inhibition of the delivery of the pacing pulse. By virtue of and in accordance with one aspect of the present invention, a means is provided to detect this sub-threshold signal and let the system respond accordingly.

To that end, the system establishes a window during a time period before the delivery of the pacing pulse and samples the intrinsic cardiac signal within the window. The system calculates referencing values from the amplitude and variation of the signals before each pacing pulse. Then the system samples the intrinsic signal just before delivering the pacing pulse. The data is compared with the referencing values. If the difference is larger than a pre-defined threshold, it predicts that the next paced event will be a fusion or pseudo-fusion beat and the system delivers a high output amplitude pacing pulse to assure capture instead of a pacing pulse of normal operating output amplitude. Since capture is assured, the system does not need to confirm capture. Instead, the system collects the evoked response of the T-wave to confirm the fusion beat. Such confirmation is made possible through morphology analysis, such as by noting a T-wave amplitude that is significantly decreased or a change in morphology.

When this condition occurs continuously, the system may adjust the pacing timing based on the desired pacing or intrinsic preference. That is, if a higher degree of pacing is desired for the patient, the device may decrease the AV/PV delay and/or increase the pacing rate, for example. Conversely, if a higher degree of intrinsic activity is desired for the patient, the device may increase the AV/PV delay and/or decrease the pacing rate, for example. When employed during capture threshold management, for example, the result is that fusion beats are taken out of the capture threshold management type of algorithms and thus, the performance and reliability of these algorithms are enhanced.

Figure 3:
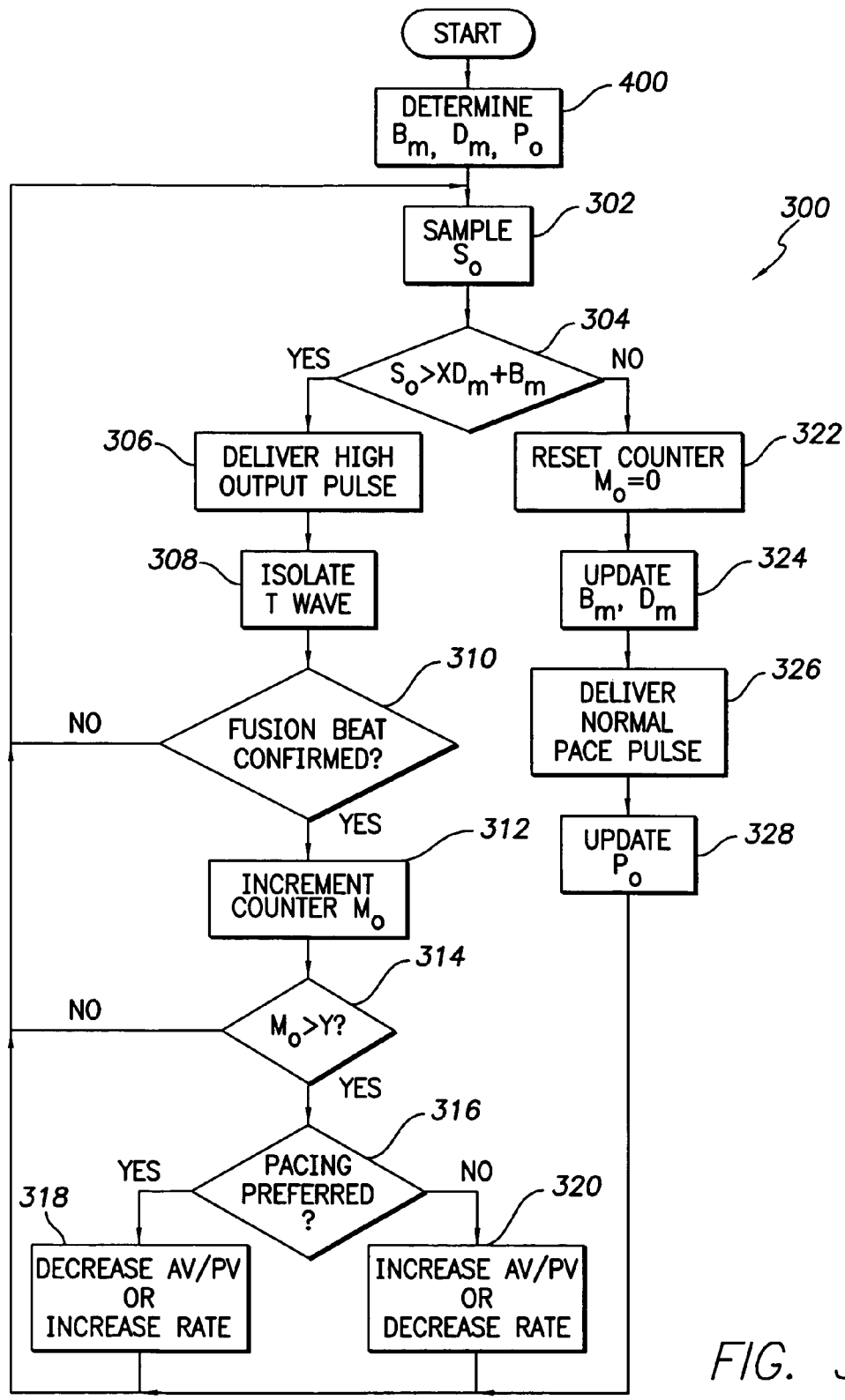
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Before the flow chart of FIG. 3 is described, reference is once again directed to FIG. 2 for a brief description of various functional elements which are employed in this embodiment. It will be noted that the device 10 further includes a fusion beat predicting circuit 61, a fusion beat control circuit 62, and a fusion beat confirmation circuit 63. While each of these elements is referred to as a "circuit", it may be appreciated that these elements may be in discrete circuit form or implemented as stages by the programmable micro-controller pursuant to performed operating instructions. As may be further noted in FIG. 2, the device includes a pacing parameter modifier 64 and an arithmetic logic unit (ALU) 65.

The fusion beat predictor 61 determines fusion beat prediction threshold values and uses them to predict if a next scheduled pacing pulse will likely be a fusion beat. The fusion beat control 62 responds to the fusion beat prediction by causing the device to deliver either a standard operating amplitude pacing pulse when a next paced event is not predicted to likely be a fusion beat or a high output amplitude pacing pulse (of sufficient amplitude to assure capture) when a next scheduled paced event is predicted to likely be a fusion beat. If a fusion beat is predicted, the fusion beat confirmation circuit 63 confirms the fusion beat after the high output pacing pulse is delivered. The confirmation may be, and in accordance with this embodiment is, based upon T wave morphology. This may be accomplished, for example, by the morphology detector 66 isolating and measuring the T wave and the confirmation circuit comparing that measurement to a threshold. The ALU 65 is provided to implement the arithmetic functions required to calculate the threshold values and threshold updates.

Referring now to FIG. 3, it is a flow chart 300 describing an overview of the operation of one embodiment of the present invention. The process of FIG. 3 initiates with the subroutine 400 wherein certain threshold values are first determined. The threshold values include: $B_m$, an average of mean EGM baselines values over N cardiac cycles; $D_m$, an average maximum EGM deflection over the N cardiac cycles; and $P_o$, an averaged T wave morphology over the N cardiac cycles. As will be seen, these values are updated as the process cycles.

The threshold values are determined over N cardiac cycles of normal pacing, that is, when a pacing pulse having a regularly operating output is to be delivered. This is contrasted with the exceptional pacing pulses to be delivered when a next paced event is predicted to likely be a fusion beat. The output of the exceptional pacing pulses is selected to be higher than that of the standard pacing pulses and more particularly, high enough to assure capture.

Figure 4:
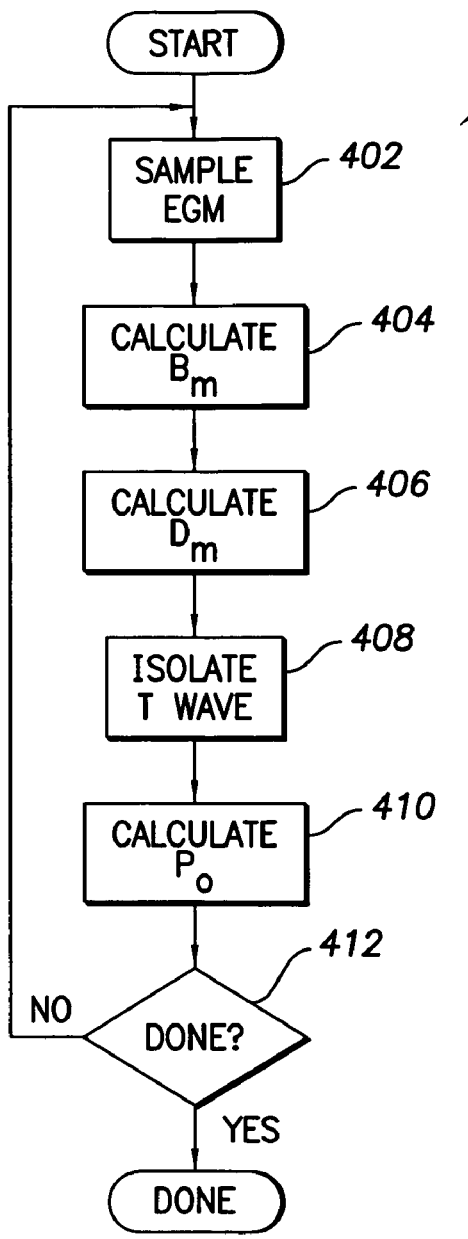
FIG. 4 is a flow chart describing the subroutine 400 of FIG. 3 wherein certain threshold values may be determined according to one embodiment of the invention.

As may be noted in FIG. 4, the subroutine 400 initiates with activity block 402 wherein the EGM is collected by the data acquisition system 90. As the EGM is collected, the ALU 65 is employed by the fusion beat predictor 61 to calculate a mean baseline value $B_o$ and average it with previous values to calculate $B_m$ according to activity block 404 for the EGM between times $t_0$ and $t_1$. Similarly, the ALU 65 is employed by the fusion beat predictor 61 to calculate a maximum baseline deviation and average it with previous values to calculate $D_m$ according to activity block 406 for the EGM between times $t_0$ and $t_1$. The morphology detector may be used to measure the EGM between times $t_0$ and $t_1$ for this purpose. These times are graphically illustrated in the timeline 440 of FIG. 5. The window of $t_0$ to $t_1$ may begin ($t_0$), for example, 15 mS before the scheduled pacing pulse and end ($t_1$) for example, 5 mS before the scheduled pacing pulse. After the device delivers a regular pacing pulse at its scheduled delivery time $t_3$, the fusion beat predictor 61 employs the morphology detector 66 again to isolate the resulting T wave and create a T wave template according to activity block 408. It then causes the ALU 66 to generate an averaged T wave template $P_o$ according to activity block 412.

The subroutine then advances to decision block 412. Here, the fusion beat detector determines if the threshold value determinations are complete. In accordance with this embodiment, if for example, N is equal to ten, if ten cardiac cycles have been processed as describes above to generate the initial values of $B_m$, $D_m$, and $P_o$, the subroutine 400 completes. If not, the subroutine returns to activity block 402.

Returning now to FIG. 3, after the initial threshold values are determined, in a next cardiac cycle, the process proceeds to activity block 302 wherein the EGM is sampled at time $t_2$ (FIG. 5) to derive sample value $S_o$. The sampling time $t_2$ may be, for example, 2 mS before the scheduled pacing pulse. Next, in decision block 304, the fusion beat detector 61 determines if the next paced event is likely to be a fusion beat. More specifically, the fusion beat detector 61 causes the ALU determine if the signal sample ($S_o$) is greater than the average mean baseline ($B_m$) plus a multiple (x) of the average maximum baseline deviation ($D_m$). If it is, the fusion beat detector declares that the next paced event is likely to be a fusion beat and directs the process to activity block 306. If not, the process is directed to activity block 322.

Figure 5:
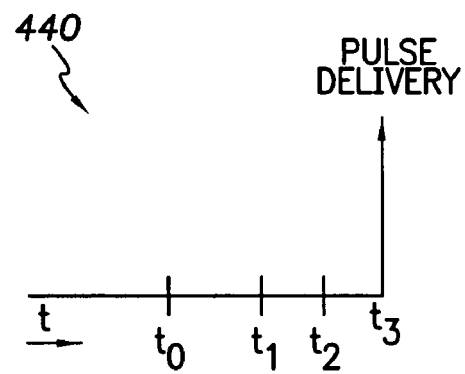
FIG. 5 is a time line corresponding to the flow chart of FIG. 4.

In activity block 306, the fusion beat control 62 causes an exceptional pacing pulse to be delivered at the regularly scheduled delivery time $t_3$ (FIG. 5). As previously mentioned, the exceptional pacing pulses have an output sufficient to assure capture.

Next, in activity block 308, the morphology detector isolates and creates a template of the resulting T wave. Then, in decision block 310, the fusion beat confirmation circuit 63 compares the template to the averaged T wave template ($P_o$). If the difference is larger than a predetermined limit, the fusion beat is confirmed. If not, the process returns to activity block 302.

If in decision block 310 the fusion beat is confirmed, the process advances to activity block 312 where a counter (not shown) of ALU 65 is incremented. Next, the ALU 65 determines if the counter is greater then a predetermined number ($M_o$). If not, the process returns to activity block 302. If it is, the process advances to decision block 316 to determine if the device has been programmed to prefer pacing of the patient. If so, the process advances to activity block 318 wherein the pacing parameter modifier 64 modifies the pacing parameters to further promote pacing of the patient. To that end, the pacing parameter modifier 64 may decrease the AV/PV delay and/or increase the pacing rate. If pacing is not preferred over intrinsic activity of the patient, the pacing parameter modifier may increase the AV/PV delay and/or decrease the pacing rate. The changes in the pacing parameters will serve to vary device timing and decrease the potential of further fusion beats. Once the pacing parameter(s) is (are) modified, the process returns to activity block 302.

If in decision block 304 it is determined that the next paced event is not likely to be a fusion beat, the process advances to activity block 322 to reset the ALU counter to zero. Hence, the pacing parameters are modified only if the predetermined number ($M_o$) of cycles having a paced event predicted to likely be a fusion beat are consecutive. Next, in activity block 324, $B_m$ and $D_m$ are updated. More particularly, for each subsequent new normal pacing pulse, the system dynamically updates the $D_m$ and $B_m$ with the new values ($B_{n+1}$ and $D_{n+1}$) measured using the weighing factor of 1/N, i.e., $B_m=B_m*(N-1)/N+B_{n+1}/N$. $D_m=D_m*(N-1)/N+D_{n+1}/N$.

Next, in activity block 326, a regular normal pacing pulse is delivered at the scheduled delivery time ($t_3$). Then, in activity block 328, the T wave template ($P_o$) is updated before the process returns to activity block 302.

The process just described is particularly useful for auto-capture assessment and threshold searches. It eliminates the need for back-up pulses which may otherwise result from false negatives, minimizes the effect of fusion beats on the outcome, and further reduces the likelihood of fusion beats themselves.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   a sensing circuit adapted to sensed intrinsic cardiac electrical signals and evoked response cardiac electrical signals;
   a pulse generator adapted to provide first and second pacing pulses to a chamber of a heart, the first pacing pulses having a normal operating output level and the second pacing pulses having an output level greater than the normal operating output level;
   a fusion beat predicting circuit operative to predict when delivery of a first pacing pulse to the chamber will likely produce a fusion beat, the prediction based on intrinsic cardiac electrical signals sensed during a time period prior to when the pulse generator will deliver the first pacing pulse; and
   a fusion beat control that causes the pulse generator to provide the second pacing pulse to the chamber in place of the first pacing pulse, in response to the fusion beat predicting circuit predicting that delivery of a first pacing pulse to the chamber will likely produce a fusion beat.

2. The device of claim 1, wherein the output level of the second pacing pulses is sufficient to assure capture.

3. The device of claim 1, wherein the sensing circuit is adapted to generate an electrogram signal representing intrinsic activity of the chamber, and the fusion beat predicting circuit obtains a signal sample of the electrogram signal prior to when the pulse generator would provide a first pacing pulse and compares the signal sample to a threshold to predict when delivery of a first pacing pulse to the chamber will likely produce a fusion beat.

4. The device of claim 3 wherein the fusion beat predicting circuit establishes a sampling window prior to when the pulse generator would provide a first pacing pulse, determines a sampling window mean potential baseline and sampling window mean potential maximum deviation, and determines the threshold from the sampling window mean potential baseline and sampling window mean potential maximum deviation.

5. The device of claim 1, further comprising a fusion beat confirmation circuit that confirms the predicted fusion beat after the second pacing pulse is provided to the chamber, the confirmation based on evoked-response cardiac electrical signals sensed during a time period after delivery of the second pacing pulse.

6. The device of claim 5, further comprising a morphology detector adapted to provide evoked-response T-wave morphology data and, wherein the fusion beat confirmation circuit confirms the predicted fusion beat based upon the T wave morphology data.

7. The device of claim 5, further comprising a pacing parameter modifier that modifies pacing parameters of the device when the confirmation circuit confirms a predetermined number of consecutive fusion beats.

8. The device of claim 7, further comprising a timing control adapted to provide pacing parameters including AV/PV interval and/or pacing rate, wherein the pacing parameter modifier modifies AV/PV interval and/or pacing rate.

9. The device of claim 1, wherein the fusion beat control causes the pulse generator to provide a first pacing pulse to the chamber in response to the fusion beat predicting circuit predicting that delivery of a first pacing pulse to the chamber will likely not produce a fusion beat.

10. An implantable cardiac stimulation device comprising:
    a pulse generator adapted to provide first and second pacing pulses to a chamber of a heart, the first pacing pulses having a normal operating output level and the second pacing pulses having an output level greater than the normal operating output level and sufficient to assure capture;
    a fusion beat predicting circuit that predicts when a next paced event of the chamber will likely be a fusion beat based on intrinsic cardiac electrical signals sensed during a time period prior to the next paced event; and
    a fusion beat control that causes the pulse generator to provide the second pacing pulse to the chamber in response to the fusion beat predicting circuit predicting that a next paced event will likely be a fusion beat and to provide the first pacing pulse to the chamber in response to the fusion beat predicting circuit predicting that a next paced event will likely not be a fusion beat.

11. The device of claim 10, further comprising a sensing circuit that generates an electrogram signal representing intrinsic activity of the chamber, wherein the fusion beat predicting circuit obtains a signal sample of the electrogram signal prior to the next paced event and compares the signal sample to a threshold to predict when a next paced event of the chamber will likely be a fusion beat.

12. The device of claim 11 wherein the fusion beat predicting circuit establishes a sampling window prior to each next paced event, determines a sampling window mean potential baseline and sampling window mean potential maximum deviation, and determines the threshold from the sampling window mean potential baseline and sampling window mean potential maximum deviation.

13. The device of claim 10, further comprising a sensing circuit that generates an electrogram signal representing evoked-response activity of the chamber; and a fusion beat confirmation circuit that confirms the predicted fusion beat based on evoked-response activity after the second pacing pulse is provided to the chamber.

14. The device of claim 13, further comprising a morphology detector adapted to provide T-wave morphology data and, wherein the fusion beat confirmation circuit confirms the predicted fusion beat based upon the T wave morphology data.

15. The device of claim 13, further comprising a pacing parameter modifier that modifies pacing parameters of the device when the confirmation circuit confirms a predetermined number of consecutive fusion beats.

16. The device of claim 15, further comprising a timing control adapted to provide pacing parameters including AV/PV interval and/or pacing rate, wherein the pacing parameter modifier modifies AV/PV interval and/or pacing rate.

17. A method comprising:
sensing intrinsic cardiac electrical signals from a chamber of the heart for a time period prior to when a first pacing pulse of a first energy level is to be delivered to the chamber of the heart;
processing the sensed intrinsic cardiac electrical signals to predict if delivery of a first pacing pulse to the chamber will likely produce a fusion beat; and
in place of a first pacing pulse, providing a second pacing pulse of a second energy level greater than the first energy level to the chamber when it is predicted that delivery of a first pacing pulse to the chamber will likely produce a fusion beat.

18. The method of claim 17, wherein processing comprises obtaining a signal sample of the sensed intrinsic cardiac electrical signals and comparing the signal sample to a threshold.

19. The method of claim 17, further comprising:
sensing evoked-response cardiac electrical signals from the chamber of the heart for a time period following delivery of the second pacing pulse; and
processing the sensed evoked-response cardiac electrical signals to confirm the predicted fusion beat.

20. The method of claim 17, further comprising providing a first pacing pulse to the chamber when it is predicted that delivery of the first pacing pulse to the chamber will not likely produce a fusion beat.

* * * * *